United States Patent
Ni et al.

(10) Patent No.: US 11,327,198 B2
(45) Date of Patent: May 10, 2022

(54) CT INSPECTION SYSTEM AND CT IMAGING METHOD FOR A RECIPROCATING SWINGING PROCESS OF A RADIOACTIVE SOURCE DEVICE AND A DETECTION DEVICE AROUND AN OBJECT AT NON-UNIFORM SPEED TO COLLECT EFFECTIVE DETECTION DATA

(71) Applicants: TSINGHUA UNIVERSITY, Beijing (CN); NUCTECH COMPANY LIMITED, Beijing (CN)

(72) Inventors: Xiulin Ni, Beijing (CN); Jianmin Li, Beijing (CN); Haitian Tan, Beijing (CN); Yulan Li, Beijing (CN); Weifeng Yu, Beijing (CN); Yuanjing Li, Beijing (CN); Hejun Zhou, Beijing (CN); Zhiqiang Chen, Beijing (CN); Chunguang Zong, Beijing (CN); Li Zhang, Beijing (CN)

( * ) Notice: Subject to any disclaimer, the term of this patent is extended or adjusted under 35 U.S.C. 154(b) by 0 days.

(21) Appl. No.: 16/234,621

(22) Filed: Dec. 28, 2018

(65) Prior Publication Data

US 2019/0204242 A1    Jul. 4, 2019

(30) Foreign Application Priority Data

Dec. 28, 2017 (CN) .......................... 201711451934.7

(51) Int. Cl.
   *G01N 23/046* (2018.01)
   *G01V 5/00* (2006.01)
   (Continued)

(52) U.S. Cl.
   CPC .............. *G01V 5/005* (2013.01); *A61B 6/032* (2013.01); *A61B 6/035* (2013.01); *A61B 6/44* (2013.01);
   (Continued)

(58) Field of Classification Search
   CPC ........... A61B 6/032; A61B 6/035; A61B 6/44; A61B 6/4429; A61B 6/4435;
   (Continued)

(56) References Cited

U.S. PATENT DOCUMENTS 6,233,308 B1 * 5/2001 Hsieh ..................... A61B 6/032
                                                  378/19
6,269,140 B1 * 7/2001 Takagi ................... A61B 6/032
                                                  378/8
(Continued)

FOREIGN PATENT DOCUMENTS

CN         1238669 A       12/1999
CN       201253215 Y        6/2009
(Continued)

OTHER PUBLICATIONS

EP Office Action dated May 23, 2019 in the corresponding EP application (application No. 19150075.0).
Office Action of EP App No. 19150075.0.

*Primary Examiner* — Allen C. Ho
(74) *Attorney, Agent, or Firm* — Kilpatrick Townsend & Stockton, LLP

(57) ABSTRACT

The present disclosure relates to the technical field of CT detection, in particular to a CT inspection system and a CT imaging method. The CT inspection system provided by the present disclosure includes a scanning device and an imaging device, wherein the scanning device having a radioactive source device and a detection device is configured to rotate at a nonuniform speed in at least partial process of scanning an object to be detected; and the imaging device generates a CT image based on effective detection data, wherein the effective detection data refer to data acquired each time the detection device rotates by a preset angle. In the present disclosure, the imaging device of the CT inspection system generates a CT image based on data acquired each time the (Continued)

detection device rotates by a preset angle, which, compared with traditional image collection solutions, can effectively reduce image deformation and improve accuracy of detection results.

8 Claims, 2 Drawing Sheets

(51) Int. Cl.
  *A61B 6/03* (2006.01)
  *A61B 6/00* (2006.01)
  *G01N 23/18* (2018.01)
(52) U.S. Cl.
  CPC .......... *A61B 6/4429* (2013.01); *A61B 6/4435* (2013.01); *A61B 6/4441* (2013.01); *A61B 6/4447* (2013.01); *G01N 23/046* (2013.01); *G01N 23/18* (2013.01); *G01N 2223/401* (2013.01)
(58) Field of Classification Search
  CPC ....... A61B 6/4441; A61B 6/4447; A61B 6/52; A61B 6/5205; G01N 23/046; G01N 23/18; G01V 5/005
  USPC ...... 378/8, 15, 19, 57, 58, 95, 196, 197, 16, 378/91, 20
  See application file for complete search history.

(56) References Cited

U.S. PATENT DOCUMENTS

| | | | | |
|---|---|---|---|---|
| 7,376,214 | B2 * | 5/2008 | Klingenbeck-Regn | A61B 6/4441 378/8 |
| 7,724,866 | B2 * | 5/2010 | Naidu | G01T 1/2985 378/15 |
| 7,817,773 | B2 * | 10/2010 | Stanton | A61B 6/466 378/15 |
| 7,881,426 | B2 * | 2/2011 | Basu | A61B 6/027 378/98.12 |
| 8,094,774 | B2 * | 1/2012 | Noshi | G06T 11/006 378/15 |
| 8,094,775 | B2 * | 1/2012 | Noshi | A61B 6/06 378/15 |
| 8,170,175 | B2 * | 5/2012 | Kasuya | A61B 6/56 378/15 |
| 8,213,568 | B2 * | 7/2012 | Heuscher | A61B 6/542 378/15 |
| 8,451,972 | B2 * | 5/2013 | Dafni | A61B 6/032 378/11 |
| 8,475,041 | B2 * | 7/2013 | Takemoto | A61B 6/548 378/197 |
| 8,489,175 | B2 * | 7/2013 | Schönborn et al. | A61B 6/4441 378/11 |
| 8,538,505 | B2 * | 9/2013 | Brunner | A61B 6/032 378/9 |
| 8,681,933 | B2 * | 3/2014 | Suzuki | A61B 6/032 378/20 |
| 8,693,621 | B2 * | 4/2014 | Thran | A61B 6/4021 378/17 |
| 8,842,804 | B2 * | 9/2014 | Ooshima | A61B 6/027 378/15 |
| 9,036,770 | B2 * | 5/2015 | Funk | G01N 23/046 378/16 |
| 9,066,687 | B2 * | 6/2015 | Vlachomitrou | A61B 6/14 |
| 9,084,543 | B2 * | 7/2015 | Kobayashi | A61B 6/032 |
| 9,155,508 | B2 * | 10/2015 | Ueki | A61B 6/4028 |
| 9,420,974 | B2 * | 8/2016 | Ye | A61B 6/5235 |
| 9,420,980 | B2 * | 8/2016 | Dong | A61B 6/547 |
| 9,538,976 | B2 * | 1/2017 | Keall | A61B 6/541 |
| 9,599,578 | B2 * | 3/2017 | Yanagita | G01N 23/046 |
| 9,662,075 | B2 * | 5/2017 | Liu | A61B 6/032 |
| 9,664,587 | B2 * | 5/2017 | Lou | G01N 23/046 |
| 9,848,835 | B2 * | 12/2017 | Berkus | A61B 6/541 |
| 10,016,171 | B2 * | 7/2018 | Fortuna | A61B 6/4488 |
| 10,101,284 | B2 * | 10/2018 | Koike | G01N 23/046 |
| 10,111,639 | B2 * | 10/2018 | Karahashi | A61B 6/54 |
| 10,143,427 | B2 * | 12/2018 | Smith | H02K 11/20 |
| 10,201,322 | B2 * | 2/2019 | Xing | A61B 6/032 |
| 10,349,909 | B2 * | 7/2019 | Okerlund | A61M 5/007 |
| 10,357,222 | B2 * | 7/2019 | Hirayu | A61B 6/54 |
| 10,537,297 | B2 * | 1/2020 | Hagiwara | A61B 6/54 |
| 10,677,943 | B2 * | 6/2020 | Moore | G01N 23/046 |
| 10,722,188 | B2 * | 7/2020 | Goto | A61B 6/469 |
| 10,799,198 | B2 * | 10/2020 | Ahn | A61B 6/542 |
| 10,935,691 | B2 * | 3/2021 | Kang | G01N 23/046 |
| 11,022,569 | B2 * | 6/2021 | Kang | G01N 23/046 |
| 2009/0003515 | A1 | 1/2009 | Naidu et al. | |
| 2010/0215144 | A1 | 8/2010 | Basu et al. | |
| 2017/0045464 | A1 | 2/2017 | Funk | |

FOREIGN PATENT DOCUMENTS

| | | |
|---|---|---|
| CN | 101683271 A | 3/2010 |
| CN | 102359971 A | 2/2012 |
| CN | 104799878 A | 7/2015 |
| CN | 105806658 A | 8/2016 |
| CN | 108120729 A | 6/2018 |
| CN | 108226195 A | 6/2018 |
| CN | 207816864 U | 9/2018 |
| CN | 207816865 U | 9/2018 |
| EP | 2990834 A1 | 3/2016 |
| JP | H11295243 A | 10/1999 |
| WO | 9919692 A1 | 4/1999 |

* cited by examiner

CT INSPECTION SYSTEM AND CT IMAGING METHOD FOR A RECIPROCATING SWINGING PROCESS OF A RADIOACTIVE SOURCE DEVICE AND A DETECTION DEVICE AROUND AN OBJECT AT NON-UNIFORM SPEED TO COLLECT EFFECTIVE DETECTION DATA

CROSS-REFERENCES TO RELATED APPLICATIONS

The present disclosure claims the priority of Chinese Application No. 201711451934.7, filed in the Chinese Patent Office on Dec. 28, 2017, whose entire contents are herein incorporated by reference.

FIELD

The present disclosure relates to the technical field of CT detection, In particular to a CT inspection system and a CT imaging method.

BACKGROUND

Except for applications in the medical field, a CT inspection system is also widely applied in the technical field of object detection, and the CT inspection system can detect not only such smaller objects as luggage and flight cases, but also such bigger objects as containers and vehicles. When working, the CT inspection system scans an object to be detected via a radiation source which is configured to generate high-energy X rays and a detection device which is configured to receive X rays penetrating through the object to be detected. The CT inspection system reflects density distribution changes of the object to be detected according to strength changes of X rays, and transforms strength changes of rays into image grayscales to obtain a perspective image of the object to be detected.

At present, the radiation source and detection device of the CT inspection system usually rotate during scanning the object to be detected. Furthermore, acceleration usually exits in the rotating process, that is, the radiation source and the detection device usually rotate at a non-uniform speed during the scanning process. Based on this current conventional image collection solution, a reconstructed CT image is deformed, which influences the accuracy of detection results.

SUMMARY

One technical problem to be solved in the present disclosure is as follows: the CT image reconstructed by the existing CT inspection system which rotates at a non-uniform speed when scanning an object to be detected is deformed, and the accuracy of detection results is poor.
[0006] In order to solve the above technical problem, a first aspect of the present disclosure provides a CT inspection system which includes a scanning device and an imaging device, wherein the scanning device is provided with a radioactive source device and a detection device, and is configured to rotate at a non-uniform speed in at least partial process of scanning an object to be detected; and the imaging device is configured to generate a CT image based on effective detection data, wherein the effective detection data refer to data acquired each time the detection device rotates by a preset angle.

According to some embodiments of the disclosure, the CT inspection system further includes a rotation monitoring device, the rotation monitoring device is configured to detect a rotating angle of the scanning device and send a signal to the imaging device each time the detection device rotates by the preset angle, and the imaging device is configured to determine the effective detection data according to signals sent by the rotation monitoring device.

According to some embodiments of the disclosure, the rotation monitoring device comprises a position detection device and a rotation control device, the position detection device IS configured to detect the position of the scanning device when the scanning device scans the object to be detected, and according to detection results of the position detection device, the rotation control device IS configured to determine a rotation angle of the scanning device, and send a signal to the imaging device each time the scanning device rotates by the preset angle.

According to some embodiments of the disclosure, the imaging device comprises a data collecting and selecting device and an image processing device, the data collecting and selecting device IS configured to acquire the effective detection data and transmit the effective detection data to the image processing device, and the image processing device IS configured to generate a CT image based on the effective detection data transmitted by the data collecting and selecting device.

According to some embodiments of the disclosure, a rotation monitoring device of the CT inspection system is configured to send a signal to the data collecting and selecting device each time the detection device rotates by the preset angle, and the data collecting and selecting device is configured to receive data of the detection device corresponding to signals of the rotation monitoring device as the effective detection data and transmit the effective detection data to the image processing device.

According to some embodiments of the disclosure, the data collecting and selecting device comprises a data acquisition device and an image collection device, the data acquisition device is configured to acquire all the data of the detection device, and the image collection device is configured to select the effective detection data from all the data of the detection device acquired by the data acquisition device and transmit the effective detection data to the image processing device.

According to some embodiments of the disclosure, a rotation monitoring device of the CT inspection system is configured to send a signal to the data acquisition device each time the detection device rotates by the preset angle, the data acquisition device is configured to transmit the signal from the rotation monitoring device to the image collection device, and the image collection device IS configured to receive data of the detection device corresponding to the signal of the rotation monitoring device as the effective detection data and transmit the effective detection data to the image processing device.

According to some embodiments of the disclosure, the data collecting and selecting device comprises a data acquisition device and an image collection device, and the data acquisition device is configured to acquire the effective detection data and transmit the effective detection data to the image processing device via the image collection device.

According to some embodiments of the disclosure, a rotation monitoring device of the CT inspection system is configured to send a signal to the data acquisition device each time the detection device rotates by the preset angle, and the data acquisition device is configured to acquire data of the detection device when receiving signals of the rotation monitoring device as the effective detection data and transmit the effective detection data to the image processing device via the image collection device.

A second aspect of the present disclosure further provides a CT imaging method, including the following steps:

scanning an object to be detected by a radioactive source device and a detection device of a scanning device, wherein the scanning device rotates at a non-uniform speed in at least partial process of scanning; and generating a CT image by an Imaging device based on data of the detection device acquired each time the detection device rotates by a preset angle.

In the present disclosure, the imaging device of the CT inspection system generates a CT image based on data acquired each time the detection device rotates by a preset angle, which, compared with the traditional image collection solution, can effectively reduce the deformation of the image and improve the accuracy of detection results.

Other characteristics and advantages of the present disclosure will become clear after a detailed description of exemplary embodiments of the present disclosure in combination with accompanying drawings below.

BRIEF DESCRIPTION OF THE DRAWINGS

In order to more clearly describe technical solutions in embodiments of the present disclosure or in the prior art, a brief introduction will be given below on the accompanying drawings which need to be used in the description of embodiments or the prior art. Apparently, the accompanying drawings described below are merely some embodiments of the present disclosure, and for those skilled in the art, other drawings can be obtained based on these drawings without any creative effort.

DETAILED DESCRIPTION OF THE INVENTION

A clear and complete description will be given below on the technical solutions of the embodiments in the present disclosure in combination with the accompanying drawings of the embodiments in the present disclosure. Apparently, the described embodiments are merely a part, but not all, of the embodiments of the present disclosure. The description of at least one exemplary embodiment below is in fact merely descriptive, rather than serving as any limitation to the present disclosure and its application or use. Based on the embodiments in the present disclosure, all the other embodiments obtained by those skilled in the art without any creative effort shall all fall within the protection scope of the present disclosure.

The techniques, methods and devices known by those skilled in the art will possibly not be discussed in detail, however, in proper conditions, the techniques, methods and devices shall be deemed as a part of the authorized description.

When the imaging device reconstructs an image, the positions where the data of the detection device is acquired need to be known. However, the imaging device of the existing CT inspection system can only determine the position of the detection data acquired each time according to a rotation speed and an initial position when the scanning device rotates at an uniform speed, but cannot effectively determine a corresponding relationship between the acquired data of the detection device and an actual position when the rotation speed of the scanning device is changeful, as a result, a CT reconstructed image is deformed, recognition difficulty is Increased, and even the image cannot be recognized.

Figure 1:
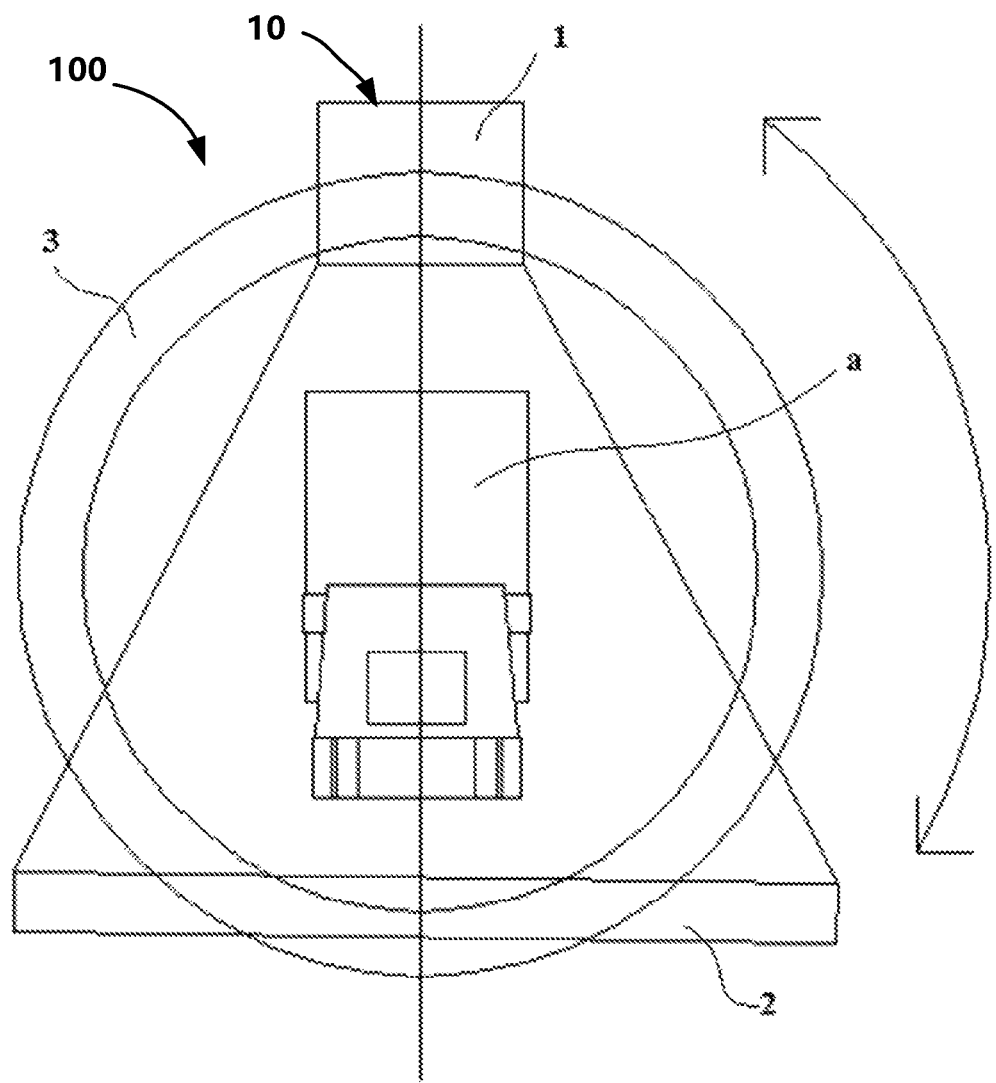
FIG. 1 shows a structural schematic diagram of a CT inspection system in one embodiment of the present disclosure.
Figure 2:
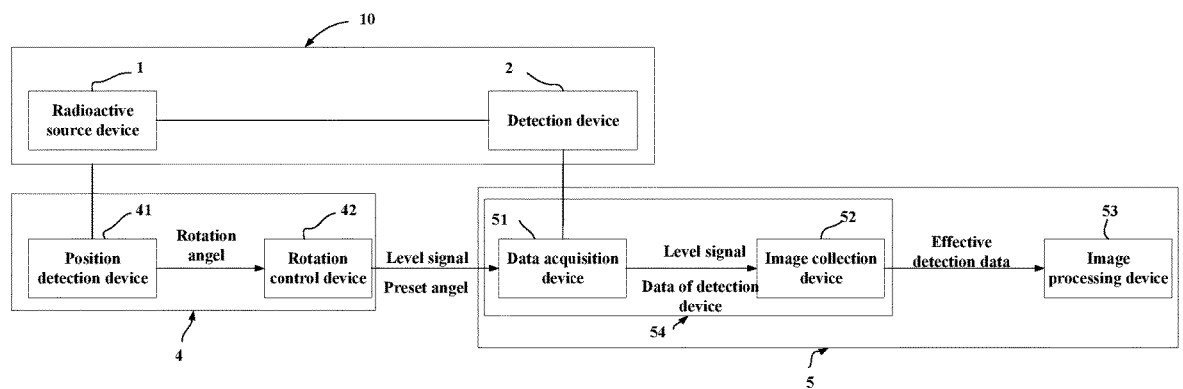
FIG. 2 shows an image generation schematic diagram of a CT inspection system as shown in FIG. 1.

In order to solve the above technical problem, the present disclosure provides a CT Inspection system, an embodiment of which is shown in FIG. 1 and FIG. 2.

Figure 3:
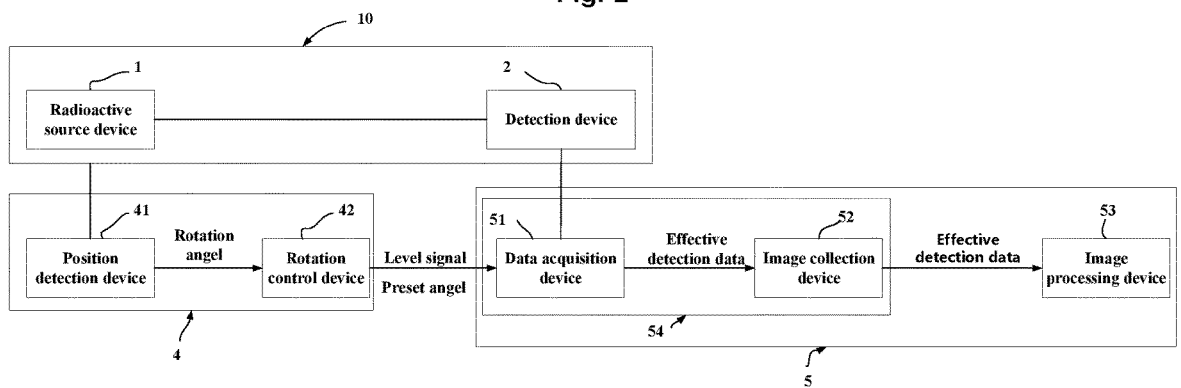
FIG. 3 shows an image generation schematic diagram of a CT inspection system in another embodiment.

With reference to FIG. 1, FIG. 2 and FIG. 3, a CT inspection system 100 provided by the present disclosure includes a scanning device 10 and an imaging device 5, wherein the scanning device 10 having a radioactive source device 1 and a detection device 2 is configured to rotate at a nonuniform speed in at least partial process of scanning an object a to be detected; and the imaging device 5 is configured to generate a CT image based on effective detection data which refer to data acquired each time the detection device 2 rotates by a preset angle.

In the present disclosure, the imaging device 5 of the CT inspection system 100 does not adopt traditional image collection solutions any longer, instead, the imaging device 5 generates a CT image based on data acquired each time the detection device 2 rotates by a preset angle (namely, effective detection data), such that the detection data which is based on to reconstruct a CT image by the imaging device 5 is all the data of the detection device 2 whose actual positions can be acquired accurately, therefore, the imaging device 5 cannot be influenced by a non-uniform rotation scanning process to reconstruct a CT image with no deformation, thereby further reducing the recognition difficulty and improving the accuracy of detection results.

As an implementation of the imaging device 5 in the present disclosure, the imaging device 5 may include a data collecting and selecting device 54 and an image processing device 53, wherein the data collecting and selecting device 54 is configured to acquire the effective detection data and transmit the effective detection data to the image processing device 53, and the image processing device 53 is configured to reconstruct a CT image based on the effective detection data transmitted by the data collecting and selecting device 54. In this way, under the coordination of the data collecting and selecting device 54 and the image processing device 53, a CT image can be conveniently reconstructed by the imaging device 5 based on the effective detection data.

In the present disclosure, in order to facilitate the imaging device 5 to recognize the effective detection data, the CT inspection system 100 may further include a rotation monitoring device 4, wherein the rotation monitoring device 4 is configured to detect a rotation angle of the scanning device 10 and send a signal to the imaging device 5 each time the detection device 2 rotates by the preset angle, and the imaging device 5 is configured to determine the effective detection data according to signals sent by the rotation monitoring device 4.

Since the rotation monitoring device 4 send a signal to the imaging device 5 each time the detection device 2 rotates by the preset angle, therefore, the imaging device 5 can recognize whether the data of the detection device 2 is the effective detection data by judging whether the data of the detection device 2 are bound with signals of the rotation monitoring device 4, which is simple and convenient, and make the recognition accuracy of effective detection data higher.

When the imaging device 5 includes a data collecting and selecting device 54 and an image processing device 53 as mentioned above, the rotation monitoring device 4 may be configured to send a signal to the data collecting and selecting device 54 each time the detection device 2 rotates by the preset angle, and the data collecting and selecting device 54 may be configured to receive data of the detection device 2 corresponding to signals of the rotation monitoring device 4 as the effective detection data and transmit the effective detection data to the image processing device 53. Based on this, the data collecting and selecting device 54 can determine data of the detection device 2 bound with signals sent by the rotation monitoring device 4 as the effective detection data, and provide the effective detection data to the image processing device 53 to reconstruct a CT image, which is convenient and efficient.

The present disclosure will be further described below in combination with the embodiment as shown in FIG. 1 and FIG. 2.

As shown in FIG. 1 and FIG. 2, in the present embodiment, a CT inspection system 100 comprises a scanning device 10, an imaging device 5, a rotation monitoring device 4, and a support 3.

The scanning device 10 is configured to scan an object a to be detected, and the scanning device 10 comprises a radioactive source device 1 and a detection device 2. The radioactive source device 1 is configured to generate X rays for penetrating through the object a to be detected. The detection device 2 is configured to receive X rays which penetrate the object a to be detected, and convert the received X rays into recordable electric signals which can be used by the imaging device to generate a CT image.

As shown in FIG. 1, the scanning device 10 of the present embodiment is arranged on the support 3, and includes a radioactive source device 1 and a detection device 2. The support 3 is circular. The radioactive source device 1 and the detection device 2 are both arranged on the support 3, and the radioactive source device I and the detection device 2 are arranged opposite to each other, such that the detection device 2 can sufficiently receive X rays sent by the corresponding radioactive source device 1. A passage for the object a to be detected exists in the middle space of the support 3. The object a to be detected passes through the middle of the circular ring, the radioactive source device 1 emits X rays to penetrate through the object a to be detected, and the X rays which penetrate through the object a to be detected are emitted to the detection device 2 opposite to the radioactive source device 1. Specifically, as can be seen from FIG. 1, in the present embodiment, the object a to be detected is a container. During each scanning, a tangent plane of the object a to be detected is disposed in the passage to be scanned by the scanning device 10. Each time the scanning of a tangent plane is finished, the object a to be detected is towed by a towing device of the CT inspection system 100 to another position at which a next tangent plane is located in the passage, so as to finish scanning of the next tangent plane. Continue like this, until the whole object a to be detected is scanned.

The radioactive source device 1 may adopt an X-ray machine or an accelerator. In the present embodiment, an accelerator serves as the radioactive source device 1. The detection device 2 is implemented by a detector array structure. In addition, although FIG. 1 only shows a group of radioactive source devices 1 and detection devices 2, it should be understood that, the scanning device 10 may include more than two groups of radioactive source devices 1 and detection devices 2.

In the present embodiment, the scanning device 10 scans the object a to be detected while swinging in a reciprocating manner. Specifically, when the object a to be detected is scanned, the radioactive source device 1 starts from an initial position, and rotates clockwise to a destination position. In this clockwise rotation process, the radioactive source device 1 continuously emits beams, until computed tomography of one tangent plane is completed. Afterwards, according to user's requirements, a towing device (not shown in the figures) tows the object a to be detected to the position of the next tangent plane. Then the radioactive source device 1 starts from the destination position and rotates anti-clockwise to the initial position again. In this anticlockwise rotation process, the radioactive source device 1 continuously emits beams, so as to finish computed tomography of the next tangent plane.

In the reciprocating swing process of the radioactive source device 1, the detection device 2 also synchronously swings in a reciprocating manner, in this way, the position on the detection device 2 covered by the ray beams generated by the corresponding radioactive source device 1 can always remain unchanged, which is conducive to ensuring that the ray beams emitted by the radioactive source device 1 are received by the detection device 2, thereby ensuring smooth realization of a scanning function of the scanning device 10.

As acceleration exists in both the radioactive source device 1 and the detection device 2 during the above reciprocating swing process, for example, acceleration exists at the beginning of the swing, and deceleration exists at the end of the swing, therefore the scanning device 10 in the present embodiment rotates at a non-uniform speed in each scanning process. In this case, if reconstructed according to traditional image collection solutions, the CT image generated by the imaging device 5 is deformed. Therefore, in order to enable the imaging device 5 to accurately reconstruct CT images and reduce image deformation, in the present embodiment, the imaging device 5 is improved, and a rotation monitoring device 4 is added. With the cooperation of the rotation monitoring device 4, the imaging device 5 of the present embodiment is capable of reconstructing CT images based on effective detection data (i.e., the data of the detection device 2 acquired each time the detection device 2 rotates by a preset angel).

The imaging device 5 and the rotation monitoring device 4 of the present embodiment will be highlighted below.

The rotation monitoring device 4 is configured to detect a rotation angle of the scanning device 10 and send a signal to the imaging device 5 each time the detection device 2 rotates by a preset angle, so as to facilitate the imaging device 5 to recognize the effective detection data and generate a CT image based on the effective detection data. As shown in FIG. 2, in the present embodiment, the rotation monitoring device 4 comprises a position detection device 41 and a rotation control device 42, wherein the position detection device 41 is configured to detect the position of the scanning device 10 when the scanning device 10 scans the object a to be detected; while the rotation control device 42 is configured to determine a rotation angle of the scanning device 10 according to detection results of the position detection device 41 and send a signal to the imaging device 5 each time the scanning device 10 rotates by the preset angle.

Specifically, the position detection device 41 may adopt a rotation displacement sensor to detect in real time the displacement by which the scanning device 10 has rotated relative to the initial position, and to feedback detection results to the rotation control device 42. Of course, the position detection device 41 may adopt other sensors, and even other detection parts. The rotation control device 42 acquires the position information of the scanning device 10 detected by the position detection device 41, and obtains the corresponding current rotation angle of the scanning device 10 after calculating. Furthermore, the rotation control device 42 is configured to control the rotation of the scanning device 10, and send a signal to the imaging device 5 each time the scanning device 10 rotates by the preset angle, so as to facilitate the imaging device 5 to distinguish the data acquired each time the detection device 2 rotates by the preset angle (namely the effective detection data) from other data. The signal sent by the rotation control device 42 each time the detection device 2 rotates by the preset angle may be a high level signal, so that the imaging device 5 can judge whether the data are effective detection data only by judging whether the corresponding data of the detection device 2 are bound with the high level signal. In addition, the preset angle is set to be 0.0001° in the present embodiment. However, it should be understood that, the preset angle may be specifically adjusted according to actual requirements.

The imaging device 5 is configured to acquire data of the detection device 2, and process the acquired data to reconstruct to reconstruct a CT image. As shown in FIG. 2, the imaging device 5 in the present embodiment includes a data collecting and selecting device 54 and an image processing device 53, and the data collecting and selecting device 54 comprises a data acquisition device 51 and an image collection device 52, wherein the data acquisition device 51 is configured to acquire all the data of the detection device 2, and the image collection device 52 is configured to select the effective detection data from all the data of the detection device 2 acquired by the data acquisition device 51, and transmit the effective detection data to the image processing device 53; and the image processing device 53 is configured to generate a CT image based on the effective detection data transmitted by the image collection device 52.

Based on the above setting, as the effective detection data are recognized not by the data acquisition device 51, but by the image collection device 52, therefore, there is no need for the data acquisition device 51 to know the current rotation position and speed of the detection device 2, but only to record all the data of the detection device 2 acquired at each pulse given by an accelerator, and send these data to the image collection device 52. In this case, the data acquisition device 51 has a simple structure and can be controlled conveniently, moreover, the existing data acquisition device 51 does not need to be changed too much, then the cost is relatively low.

Specifically, as shown in FIG. 2, a basis based on which the image collection device 52 in the present embodiment recognizes effective detection data is a signal sent by the rotation monitoring device 4 each time the detection device 2 rotates by the preset angle, that is, in the present embodiment, it's according to signals sent by the rotation monitoring device 4 each time the detection device 2 rotates by the preset angle that the image collection device 52 selects the effective detection data from all the data of the detection device 2 acquired by the data acquisition device 51.

More specifically, as can be seen from FIG. 2, in the present embodiment, the rotation monitoring device 4 sends a signal to the data acquisition device 51 each time the detection device 2 rotates by the preset angle, the data acquisition device 51 transmits the signal from the rotation monitoring device 4 to the image collection device 52, and the image collection device 52 receives data of the detection device 2 corresponding to the signal of the rotation monitoring device 4 as the effective detection data and transmits the effective detection data to the image processing device 53. In this way, in the operating process of the CT inspection system 100, each time the detection device 2 rotates by the preset angle, the rotation control device 42 sends a level signal to the data acquisition device 51, the data acquisition device 51 sends both the received level signals of the rotation control device 42 and the data of the detection device 2 acquired at the same time to the image collection device 52, and the image collection device 52 chooses data of the detection device 2 according to the level signal, wherein the image collection device 52 only determines data of the detection device 2 which are bound with high level signals as the effective detection data. After the scanning is finished, the image collection device 52 may package all the effective detection data and provide the packaged effective detection data to the image processing device 53. The image processing device 53 then finishes reconstruction of a CT image based on the effective detection data provided by the image collection device 52.

Since the corresponding relationship between the effective detection data and the actual positions is not influenced by a non-uniform rotation scanning process, and the actual positions of the effective detection data are always known, therefore, a CT image reconstructed by the imaging device based on the effective detection data is less deformed, which improves the accuracy of detection results.

With reference to FIG. 3, as an alternative embodiment of the above embodiment, the effective detection data may not be recognized by the image collection device 52, but is directly acquired by the data acquisition device 51, i.e., the data acquisition device 51 no longer acquires all the data of the detection device 2, but directly acquires the effective detection data, and then transmits the effective detection data to the image processing device 53 via the image collection device 52. In this case, the image collection device 52 only has the function of transmitting the effective detection data to the image processing device 53, but no longer has the function of recognizing the effective detection data.

In the alternative embodiment, the data acquisition device 51 may recognize the effective detection data based on signals sent by the rotation monitoring device 4 each time the detection device 2 rotates by the preset angle. Specifically, the rotation monitoring device 4 may send a signal to the data acquisition device 51 each time the detection device 2 rotates the preset angle, and the data acquisition device 51 then acquires data of the detection device 2 as effective detection data when receiving signals of the rotation monitoring device 4, and transmits the effective detection data to the image processing device 53 via the image collection device 52. More specifically, a level signal may be transmitted to the data acquisition device 51 by the rotation control device 42, and the data acquisition device 51 starts to acquire data of the detection device 2 only when receiving the level signal, and the acquired data is taken as the effective detection data and then transmitted to the image processing device 53 via the image collection device 52.

In summary, the CT inspection system 100 of the present disclosure can effectively solve the problem of deformation of CT images reconstructed during non-uniform rotation scanning process in the prior art.

Based on this, another aspect of the present disclosure further provides a CT imaging method, comprising the following steps:

scanning an object a to be detected by a radioactive source device 1 and a detection device 2 of a scanning device 10, wherein the scanning device 10 rotates at a non-uniform speed in at least partial process of scanning; and generating a CT image by an imaging device based on data of the detection device 2 acquired each time the detection device 2 rotates by a preset angle.

For the CT imaging method in the present disclosure, during a non-uniform rotation scanning of a scanning device 10, a CT image is generated no longer based on all the data of the detection device 2, but based on data acquired each time the detection device 2 rotates by a preset angle, thereby effectively reducing image deformation and improving detection accuracy.

What is described above is merely exemplary embodiments of the present disclosure, rather than a limitation to the present disclosure. Any modification, equivalent substitution and improvement made within the spirit and principle of the present disclosure shall all fall within the protection scope of the present disclosure.

What is claimed is:

1. A CT imaging method, comprising the following steps:
    scanning an object to be detected by a radioactive source device and a detection device of a scanning device, wherein the scanning device rotates at a non-uniform speed in at least partial process of scanning;
    detecting a rotating angle of the scanning device by a rotation monitoring device, and sending a signal by the rotation monitoring device to an imaging device each time the scanning device rotates by a preset angle;
    determining effective detection data by the imaging device according to the signal sent by the rotation monitoring device; and
    generating a CT image by the imaging device based on the effective detection data, wherein the effective detection data refer to data of the detection device acquired each time the scanning device rotates by the preset angle.

2. The CT imaging method according to claim 1, wherein detecting a rotating angle of the scanning device by a rotation monitoring device, and sending a signal by the rotation monitoring device to an imaging device each time the scanning device rotates by a preset angle comprises:
    detecting a position of the scanning device by a position detection device when the scanning device scans the object to be detected by a data acquisition device of a data collecting and selecting device; and
    according to detection results of the position detection device, determining the rotating angle of the scanning device, and sending a signal to the imaging device each time the scanning device rotates by the preset angle by a rotation control device of the rotation monitoring device.

3. The CT imaging method according to claim 1, wherein determining effective detection data by the imaging device according to the signal sent by the rotation monitoring device, and generating a CT image by the imaging device based on the effective detection data comprises:
    acquiring the effective detection data by a data collecting and selecting device of the imaging device, and transmitting the effective detection data by the data collecting and selecting device to an image processing device of the imaging device; and
    generating a CT image by the image processing device based on the effective detection data transmitted by the data collecting and selecting device.

4. The CT imaging method according to claim 3, wherein acquiring the effective detection data by a data collecting and selecting device of the imaging device comprises:
    receiving data of the detection device corresponding to signals of the rotation monitoring device as the effective detection data by the data collecting and selecting device.

5. The CT imaging method according to claim 3, wherein acquiring the effective detection data by a data collecting and selecting device of the imaging device, and transmitting the effective detection data by the data collecting and selecting device to an image processing device of the imaging device comprises:
    acquiring data of the detection device by a data acquisition device of the data collecting and selecting device; and
    selecting the effective detection data by an image collection device of the data collecting and selecting device from the data of the detection device acquired by the data acquisition device, and transmitting the effective detection data to the image processing device by the image collection device.

6. The CT imaging method according to claim 5, further comprising:
    transmitting the signal from the rotation monitoring device to the image collection device by the data acquisition device;
    wherein selecting the effective detection data by an image collection device of the data collecting and selecting device from the data of the detection device acquired by the data acquisition device comprises:
    receiving data of the detection device corresponding to the signal of the rotation monitoring device as the effective detection data by the image collection device.

7. The CT imaging method according to claim 3, wherein acquiring the effective detection data by a data collecting and selecting device of the imaging device, and transmitting the effective detection data by the data collecting and selecting device to an image processing device of the imaging device comprises:
    acquiring the effective detection data by a data acquisition device of the data collecting and selecting device; and
    transmitting the effective detection data by the data acquisition device to the image processing device via an image collection device of the data collecting and selecting device.

8. The CT imaging method according to claim 7, wherein acquiring the effective detection data by a data acquisition device of the data collecting and selecting device comprises:
    acquiring data of the detection device when receiving signals of the rotation monitoring device as the effective detection data by the data acquisition device.

* * * * *